United States Patent [19]

Haber et al.

[11] Patent Number: 4,935,013
[45] Date of Patent: Jun. 19, 1990

[54] COLLAPSIBLE NEEDLE COVER

[75] Inventors: Terry M. Haber, Lake Forest; Pieter Halter, Santa Ana; Clark B. Foster, El Toro, all of Calif.

[73] Assignee: Habley Medical Technology Corporation, Laguna Hills, Calif.

[21] Appl. No.: 200,361

[22] Filed: May 31, 1988

Related U.S. Application Data

[63] Continuation-in-part of Ser. No. 159,373, Feb. 23, 1988, abandoned.

[51] Int. Cl.⁵ ............................................. A61M 5/32
[52] U.S. Cl. ................................. 604/192; 604/198; 604/263
[58] Field of Search ............................. 128/760–765; 604/110, 111, 162, 163, 192, 197, 198, 117, 263; 206/365, 366

[56] References Cited

U.S. PATENT DOCUMENTS

| | | | |
|---|---|---|---|
| 3,904,033 | 9/1975 | Haerr | 604/263 |
| 4,139,069 | 2/1979 | Alvarez | 604/198 |
| 4,725,267 | 2/1988 | Vaillancourt | 604/198 |
| 4,735,618 | 4/1988 | Hagen | 604/192 |

Primary Examiner—Randall L. Green
Assistant Examiner—K. M. Reichle
Attorney, Agent, or Firm—Morland C. Fischer

[57] ABSTRACT

A safety enhancing, relatively low-cost, needle cover which is integrally bonded to a disposable needle cannula of a hypodermic syringe and adapted to eliminate the handling and/or destruction of the needle after use. The needle cover comprises distally and proximally oriented pairs of needle cover segments which are hingedly interconnected and pivotable relative to one another. The needle cover is collapsible from an open, expanded configuration, with the cannula biased in an armed state for administering an injection of the fluid contents of the syringe, to a closed, generally planar configuration, with the cannula biased in a shielded state completely surrounded, shielded and isolated after use. By virtue of the present invention, the needle cannula can be safely discarded within its collapsible cover while avoiding an accidental needle strike and the spread of a contagious, and possibly life threatening disease.

16 Claims, 3 Drawing Sheets

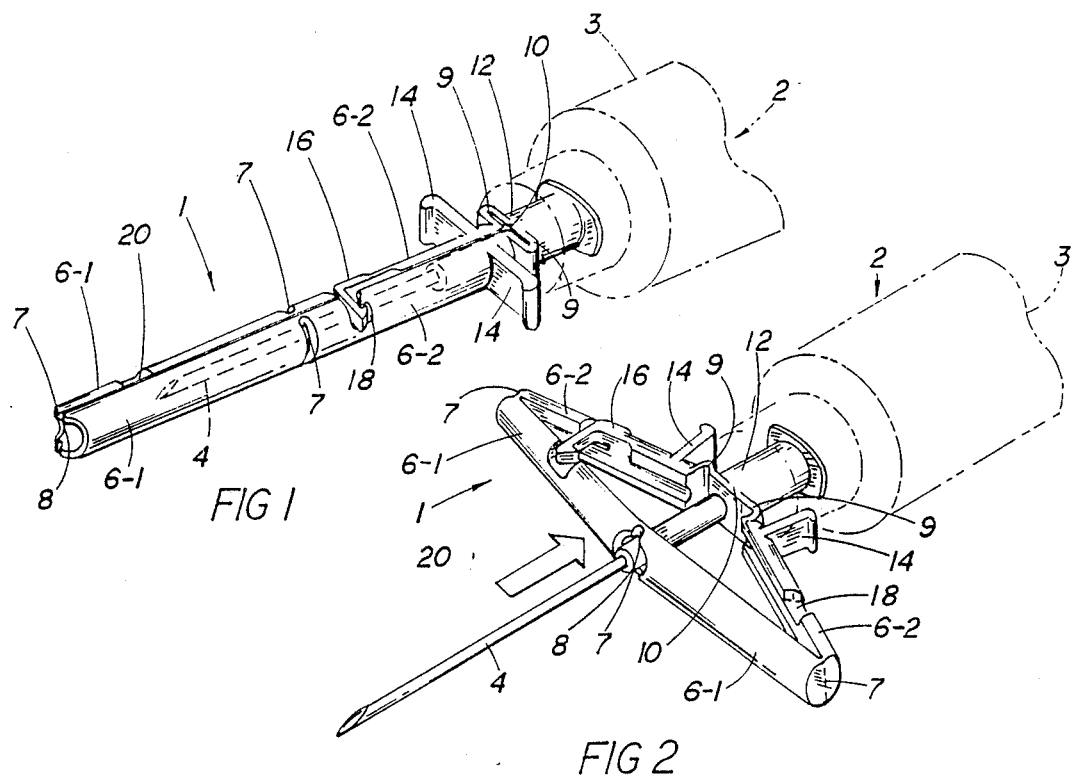
FIG 1
FIG 2
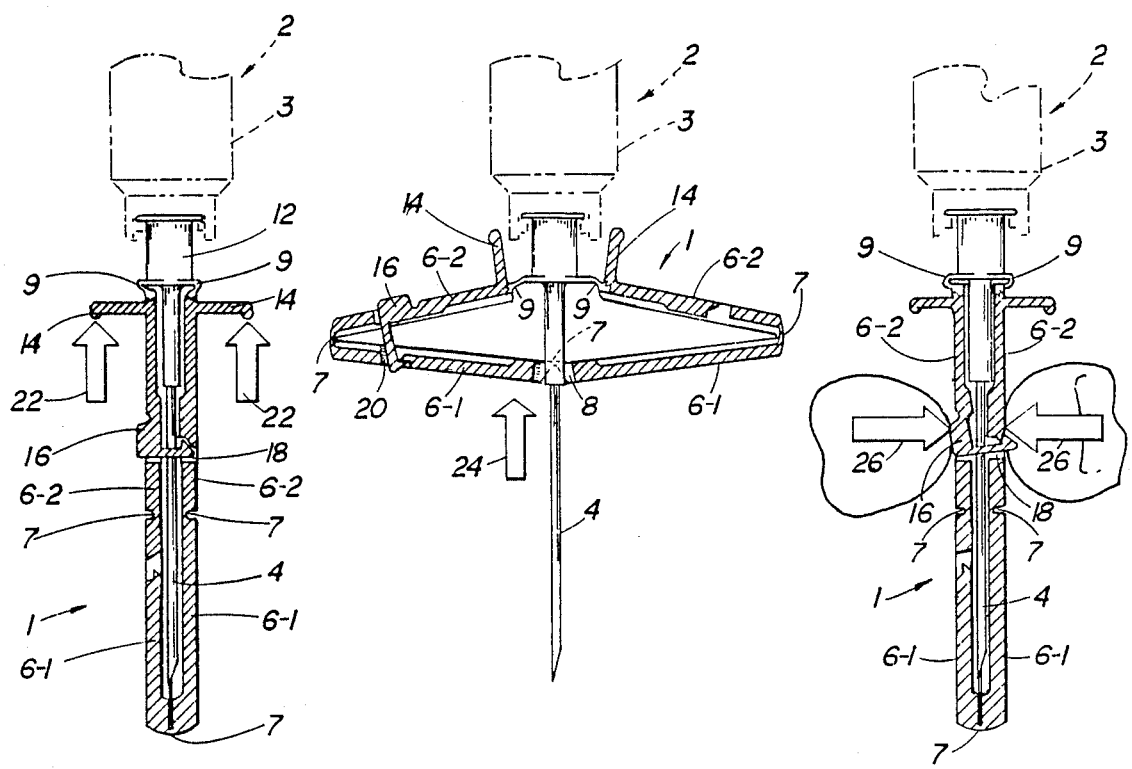
FIG 3
FIG 4
FIG 5

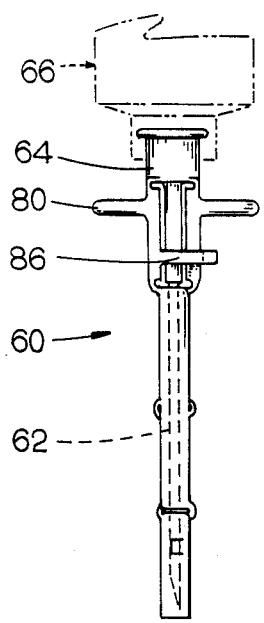
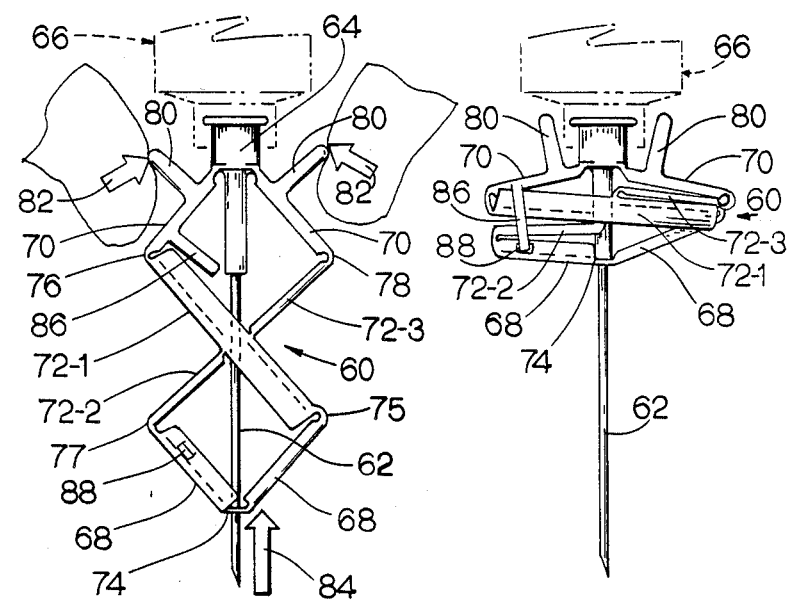
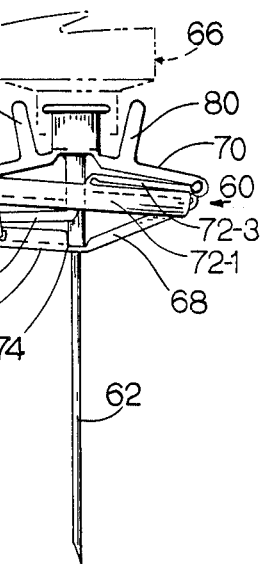
FIG 8     FIG 9     FIG 10
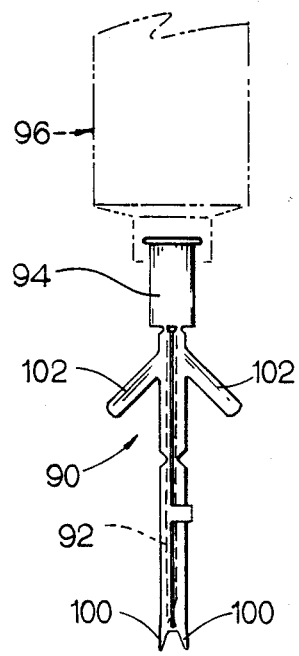
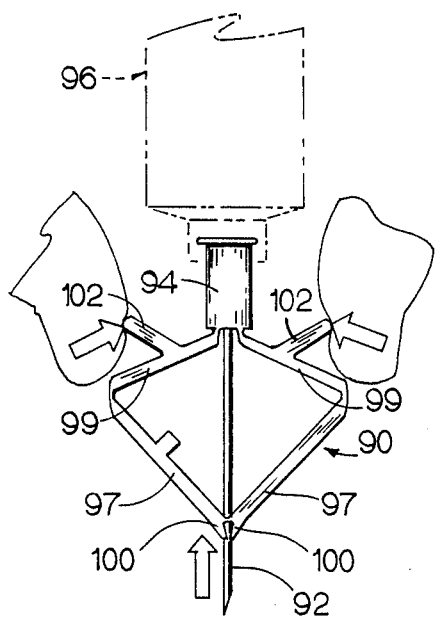
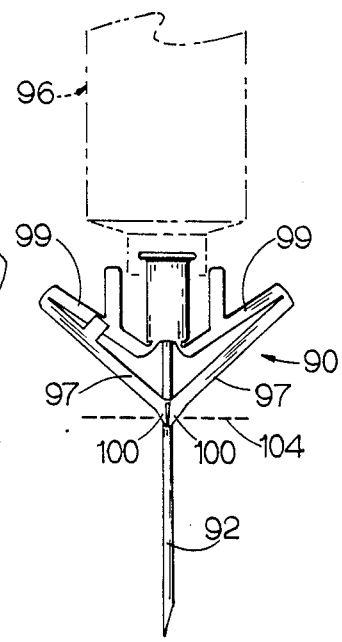
FIG 11     FIG 12     FIG 13

COLLAPSIBLE NEEDLE COVER

CROSS REFERENCE TO RELATED APPLICATIONS

This patent application is a continuation-in-part of application Ser. No. 159,373 filed Feb. 23, 1988, now abandoned.

BACKGROUND OF THE INVENTION

1. FIELD OF THE INVENTION

This invention relates to a safety enhancing and relatively low-cost needle cover which is integrally connected to a disposable needle cannula of a hypodermic syringe, wherein the cover is collapsible from an open, expanded configuration, at which the cannula is exposed for administering an injection, to a closed, generally planar configuration, at which the cannula is completely surrounded, shielded, and isolated after use.

2. PRIOR ART

Hypodermic syringes are used for a variety of purposes. By way of example, the syringe may be used to expulse fluid medication to a patient by way of a hypodermic needle cannula. However, the syringe may be used to treat a patient with a communicable disease. Prior to disposal of the syringe, the needle cannula thereof is sometimes broken to prevent reuse. Health care workers are especially susceptible to accidental and potentially infectious needle strikes due to the careless handling or breaking of the cannula and disposing of the syringe after use. The resulting mini-accidents caused by an inadvertent needle strike typically require a blood test for such diseases as AIDS and Hepatitus. The corresponding cost and inefficiency of testing health care workers who have received an inadvertent needle strike result in considerable waste, which may be particularly damaging to the health care facility which is striving for economy. In copending patent application No. 159,374 filed on Feb. 23, 1988, and entitled "COLLAPSIBLE BLOOD COLLECTOR", a safety enhancing, relatively low-cost, collapsible needle cover is described which is associated with a double-ended hypodermic needle cannula and a collapsible blood collection tube holder within which a blood sample may be automatically drawn from a patient. The present invention is directed to a collapsible needle cover which is associated with a hypodermic needle cannula and a syringe cylinder from which a fluid medication, or the like, may be expulsed to a patient.

In a search of the Patent Office records, the following U S. patents were uncovered which disclose various needle cover arrangements:

| | |
|---|---|
| 3,840,008 | October 8, 1974 |
| 3,884,230 | May 20, 1975 |
| 4,139,009 | February 13, 1979 |
| 4,303,069 | December 1, 1981 |
| 4,664,653 | May 12, 1987 |
| 4,725,267 | February 16, 1988 |
| 4,735,618 | April 5, 1988 |

SUMMARY OF THE INVENTION

In general terms, this invention relates to a safety enhancing, relatively low-cost, needle cover which is integrally bonded to and collapsible around a disposable, single use needle cannula. In a first embodiment of the invention, the combination cannula and collapsible needle cover is detachably connected to the distal bore of a hypodermic syringe. In a second embodiment, the combination cannula and collapsible needle cover is integrally connected to the distal bore of a syringe so as to form a one-piece, disposable syringe assembly.

The needle cover of the present invention comprises distally and proximally oriented pairs of needle cover segments, each of which segments being joined to an adjacent segment by means of an integral hinge around which said cover segments pivot. The needle cover is collapsible from an open, expanded configuration, at which the needle cannula is biased in an armed state for administering an injection, to a closed, generally planar configuration, at which the needle cannula is biased in a shielded state, to be completely surrounded and isolated by the cover. A pair of oppositely disposed, rotatable motion transferring arms is connected to the needle cover so that a health care worker may manually and selectively move the cover between the open and closed configurations.

A locking catch is connected to one of the needle cover segments and is adapted to move into respective engagement with adjacent cover segments to either releasably retain the needle cover in the open configuration with the cannula in the armed state or permanently lock the needle cover in the closed configuration with the cannula in the shielded state. Accordingly, the needle cannula may be safely disposed of after use within its collapsible cover to avoid subjecting the health care worker to an accidental needle strike and the spread of a contagious, and possibly life-threatening, disease.

In an additional embodiment of the invention, the needle cover may be formed from distally and proximally oriented pairs of needle cover segments and intermediate cover segments located therebetween. The cover segments are pivotally interconnected with one another at respective, integral hinges to permit the needle cover to be moved between the open, expanded configuration and the closed, substantially planar configuration. The needle cover of this embodiment is characterized by a minimized lateral width in the open configuration to facilitate the positioning of the syringe and the alignment of the needle cannula during the administration of an injection.

In yet another embodiment of the invention, the needle cover is provided with a pair of axially projecting resilient fingers which engage the needle cannula and function as spring locks to releasably retain the cover in the open, expanded configuration so that an injection may be administered. The resilient fingers slide rearwardly along the cannula to cause the needle cover to be continuously rotated and automatically snapped-locked in a swept-back, over center configuration without the addition of a separate locking element.

BRIEF DESCRIPTION OF THE DRAWINGS

FIG. 1 shows the collapsible needle cover according to a first embodiment of the invention detachably connected to the distal bore of a hypodermic syringe and moved to a closed, generally planar configuration for surrounding and shielding a disposable needle cannula;

FIG. 2 shows the collapsible needle cover of FIG. 1 in an open, generally expanded configuration to expose the needle cannula for the purpose of administering an injection of the fluid contents of the syringe;

FIGS. 3–5 illustrate the details for operating the needle cover of FIG. 1;

FIGS. 8–10 show the collapsible needle cover according to a third embodiment of the invention having a minimized lateral width when in the open, expanded configuration for administering an injection; and FIGS. 11 to 13 shows the collapsible needle cover according to a fourth embodiment of the invention having resilient fingers for automatically and reliably locking said cover in the open, expanded configuration for administering an injection.

DESCRIPTION OF THE PREFERRED EMBODIMENTS

Figure 6:
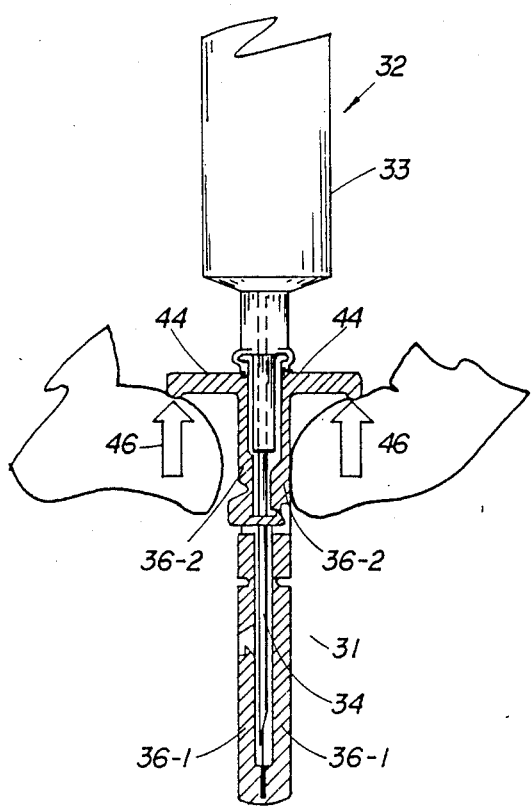
FIGS. 6 and 7 show the collapsible needle cover according to a second embodiment of the invention integrally connected to the distal bore of a hypodermic syringe to form a one-piece, disposable syringe assembly.

The collapsible needle cover according to a first embodiment of the present invention is best described while referring to FIGS. 1–5 of the drawings, where FIGS. 1 and 2 show the needle cover 1 detachably connected to the distal bore of the hollow cylinder 3 of a conventional hypodermic syringe (shown in phantom and represented by the reference numeral 2). The needle cover 1 is preferably, but not necessarily, fabricated from a radiation grade polypropylene material. FIG. 1 shows the needle cover 1 in a closed, generally planar configuration so as to completely surround, shield, and isolate a needle cannula 4 and thereby prevent an accidental needle strike and the spread of a contagious, and possibly life threatening disease. FIG. 2 shows the needle cover 1 in an open, expanded configuration to expose the cannula 4 and thereby permit said cannula to either communicate with a source of fluid (so that the syringe 2 may be infused with a medication, vitamin, or the like) or penetrate the skin of a patient (so that an injection may be administered according to medically accepted techniques). As will soon be described, the collapsible needle cover 1 and needle cannula 4 are integrally connected to one another so as to be attached to or removed from the syringe 2 as a one piece, combination cannula/cover.

Referring to concurrently to FIGS. 1 and 2, the needle cover 1 is shown comprising distally and proximally oriented pairs of needle cover segments 6-1 and 6-2. Each needle cover segment 6-1 and 6-2 is joined to its adjacent segment by means of a respective, integral hinge 7 around which the cover pivots when moving between the closed and open configurations of FIGS. 1 and 2. A narrow orifice 8 is established through the hinge 7 at the intersection of the distally oriented cover segments 6-1, so as to receive the distal end of needle cannula 4 therethrough when the needle cover 1 is moved to the open, expanded configuration of FIG. 2.

The proximally oriented pair of needle cover segments 6-2 are connected to a needle support 10 by means of integral hinges 9. A conventional luer lock fitting 12 projects proximally from the needle support 10. In the assembled relationship of FIGS. 1 and 2, the luer lock fitting 12 of needle cover 1 is interconnected (i.e. rotated into engagement) with the distal bore of the syringe cylinder 3 whereby to detachably connect the needle cover 1 to the syringe 2. The needle support 10 is integrally connected (e.g. molded or thermally bonded) to the needle cannula 4 so as to support and retain the cannula in coaxial alignment with the luer lock fitting 12 and the cylinder 3 of syringe 2. Hence, the needle cover 1 and needle cannula 4 are packed and shipped to health care facilities as a single piece, combination cannula/cover. Moreover, and in the assembled relationship, the proximal end of cannula 4 communicates with the interior with the syringe cylinder 3 via the luer lock fitting 12, whereby the cylinder may be infused with fluid or fluid may be expulsed from the cylinder (with the needle cover 1 in the open, expanded configuration of FIG. 2).

A pair of motion transferring arms 14 projects outwardly and in opposite directions from respective proximally oriented needle cover segments 6-2. As will be explained when referring to FIG. 4 the motion transferring arms 14 may be manually rotated towards one another, whereby to cause the needle cover segments 6-1 and 6-2 to pivot around their respective hinges 8 and 9 and thereby cause needle cover 1 to move from the closed, substantially planar configuration of FIG. 1, to the open, expanded configuration of FIG. 2, such that needle cannula 4 is biased in an armed state from a shielded state.

A locking catch 16 extends from one of the proximally oriented cover segments 6-2. A first notch 18 is formed in the other of the proximally oriented cover segments 6-2. A second notch 20 is formed in the distally oriented cover segment 6-1 which lies immediately above and is contiguous with the proximally oriented cover segment 6-2 from which locking catch 16 extends. As will also be explained while referring to FIGS. 4 and 5, the locking catch 16 performs a dual function. In a first case, locking catch 16 is rotated through notch 20 to automatically and releasably retain needle cover 1 in the open, expanded configuration of FIGS. 2 and 4 and thereby permit the cylinder 3 of syringe 2 to be infused with fluid for the purpose of administering an injection. In a second case, locking catch 16 is rotated through notch 18 to automatically lock needle cover 1 in the closed, substantially planar configuration of FIGS. 1 and 5, whereby the needle cannula 4 is surrounded, shielded, and isolated to permit the cannula to be safely handled and discarded after use while avoiding an accidental needle strike.

The operation of the collapsible needle cover 1 is now describe while referring to FIGS. 3, 4, and 5 of the drawings. FIG. 3 shows the needle cover 1 immediately after its removal from a package in which said cover is transported to a health care facility. More particularly, a pre-sterilized needle cover 1 is packed in a substantially collapsed condition with the needle cover segments 6-1 and 6-2 thereof pivoted around their respective hinges 7 and 9 to the closed, generally planar configuration to surround needle cannula 4. However, to permit the cover 1 to be moved, by a health care worker, out of the collapsed condition, whereby needle cannula 4 may be biased in the armed state (of FIG. 4) from the shielded state (of FIG. 3) so that an injection may be administered, the locking catch 16 is located next to, but outside, the notch 18 in the adjacent proximally oriented cover segment 6-2. That is to say, the needle cover 1 is moved to but not locked in the closed, generally planar configuration.

The combination needle cover 1/needle cannula 4 is removed from its package with the cover in the collapsed configuration and the needle cannula 4 in the shielded state. The cover is then removably attached to the syringe 2 by rotating the luer lock fitting 12 of the cover into engagement with the distal bore of the syringe cylinder 3.

In FIG. 4, the needle cover 1 is moved out of the collapsed condition, so that needle cannula 4 can be biased in the armed state. More particularly, with the needle cover 1 attached to the cylinder 3 of syringe 2, the health care worker applies an axially and proximally directed force to each of the pair of motion transferring arms 14 (in the direction of the reference arrows 22 of FIG. 3). Accordingly, the arms 14 will rotate towards one another in a generally proximal direction, whereby to correspondingly cause needle cover segments 6-1 and 6-2 to pivot around their respective hinges 7 and 9 for movement to the open, expanded configuration of FIG. 4. During the relocation of needle cover 1 (in the direction of reference arrow 24), the locking catch 16, which extends from a proximally oriented cover segment 6-2 is advanced through the notch 20, whereby to be automatically snapped into engagement with its adjacent, contiguously disposed and distally oriented cover segment 6-1 in which the notch 20 is formed to releasably and reliably retain needle cover 1 in the open, expanded configuration. Moreover, the distal end of needle cannula 4 extends through the opening 8 in the hinge 7 between adjacent distally oriented cover segments 6-1, so that cannula 4 is held in the armed state at which syringe cylinder 3 is infused with fluid for subsequent injection through the skin of a patient.

After an injection is administered, and referring now to FIG. 5 of the drawings, the needle cover 1 is again collapsed whereby cover segments 6-1 and 6-2 are returned to the closed, generally planar configuration and needle cannula 4 is biased in the shielded state. More particularly, the health care worker detaches the locking catch 16 from (i.e. rotates locking catch 16 out of engagement with) the distally oriented notch 20. With his thumb and index finger, the health care worker then applies equal and opposite, laterally directed forces (in the direction of the reference arrows 26) to the proximally oriented needle cover segment 6-2 to cause the segments 6-1 and 6-2 to pivot around their respective hinges 7 and 9 and thereby collapse needle cover 1 around needle cannula 4. The continued application of the laterally directed forces advances locking catch 16 through the notch 18 in the proximally oriented cover segment 6-2 in which said notch is formed.

Accordingly, locking catch 16 is automatically snapped into engagement with cover segment 6-2, whereby to permanently lock needle cover 1 in the closed, generally planar configuration with needle cannula 4 biased in the shielded state. Hence, the needle cover segments 6-1 and 6-2 surround, shield and isolate the cannula 4 so that the syringe 2 may be safely handled without subjecting the health care worker to an accidental needle strike and the spread contagious and possibly life-threatening disease. Since the locking catch 16 prevents the inadvertent return of the needle cover 1 to the open, expanded configuration (of FIG. 4), needle cover 1 may be detached from syringe cylinder 3. However, unlike many conventionally syringe assemblies, the needle cannula 4 need not be directly handled, cut, or otherwise destroyed after use, but may be conveniently and safely discarded in the shielded state of FIG. 5 within the collapsed needle cover 1.

Figure 7:
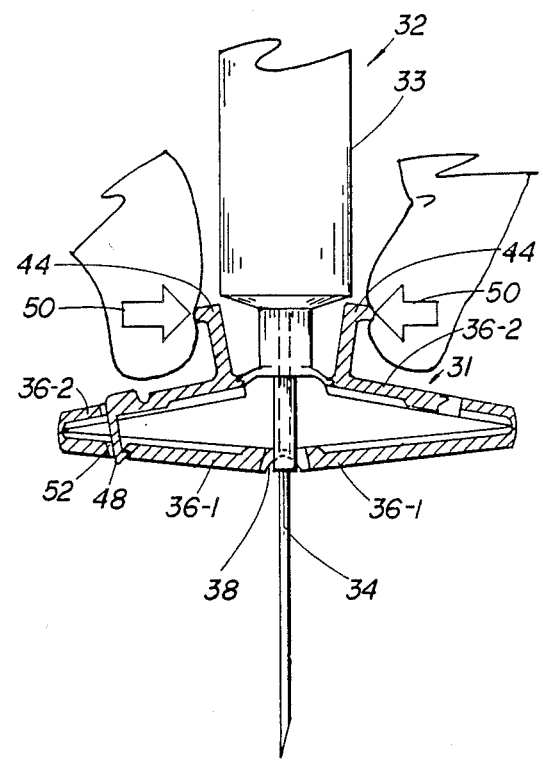

A collapsible needle cover 31 according to a second embodiment of the present invention is now described while referring to FIGS. 6 and 7 of the drawings. Like the needle cover 1 of FIGS. 1–5, the needle cover 31 of FIGS. 6 and 7 is integrally connected (e.g. molded or bonded) to a needle cannula 34. However, needle cover 31 is also integrally connected to the distal bore of a cylinder 33 from a syringe 32 so as to form a one-piece, disposable syringe assembly.

Needle cover 31 comprises distally and proximally oriented pairs of needle cover segments 36-1 and 36-2 which are hingedly interconnected with one another and adapted to pivot when cover 31 is moved between the closed and open configurations. That is, FIG. 6 shows the needle cover 36 in a closed, generally planar configuration with the needle cover segments 36-1 and 36-2 completely surrounding, shielding, and isolating the cannula 34 so as to prevent an accidental needle strike. FIG. 7 shows the needle cover 31 in the open, expanded configuration to expose the cannula 34 through an orifice 38 in the cover 31 and thereby permit the fluid contents of syringe 33 to be injected through the skin of a patient.

A pair of motion transferring arms 44 project outwardly and in opposite directions from respective proximally oriented needle cover segments 36-2. As previously disclosed when referring to FIGS. 4 and 5, axially and proximally directed forces may be manually applied to the motion transferring arms 44 (in the direction of the reference arrows 46 of FIG. 6) to cause said arms to rotate, whereby needle cover segments 36-1 and 36-2 are correspondingly pivoted around their respective hinges. Hence, the needle cover 31 is moved to the open, expanded configuration of FIG. 7 with needle cannula 34 biased in the armed state. The continued application of force to motion transferring arms 4 (in the direction of reference arrows 50) also causes a locking catch 48, which extends from a proximally oriented cover segment 36-2, to be advanced through a notch 52 and snapped into engagement with the adjacent and continuously disposed distal cover segment 36-1 in which such notch is formed. Accordingly, the needle cover 31 is releasably retained in the open, expanded configuration of FIG. 7 so that an injection may be administered.

A description of the return of needle cover 31 to the closed, generally planar configuration of FIG. 6 with needle cannula 34 in the shielded state (suitable to permit the one-piece syringe 32 of the second embodiment to be safely discarded after use) is similar to that which was previously provided when referring to FIG. 5. Therefore, for purposes of brevity, this description will be omitted.

FIGS. 8–10 of the drawings illustrate a collapsible and disposable needle cover 60 formed in accordance with a third embodiment of the present invention. It is preferable that the needle cover 60 of the present embodiment include a needle cannula 62 that is integrally connected (e.g. molded or bonded) to a needle supporting hub 64 having a luer lock fitting. Therefore, a one-piece combination needle cannula and collapsible needle cover is provided that is adapted to be removably attached to the distal end of a conventional syringe (shown in phantom and represented by the reference numeral 66), whereby cannula 62 may be shielded and removed from the syringe 60 after use to permit the cannula to be safely handled and discarded while avoiding an accidental needle strike and the possible spread of a contagious disease.

Needle cover 60 comprises distally and proximally oriented pairs of needle cover segments 68 and 70. Needle cover segments 68 and 70 are hingedly interconnected with intermediate needle cover segments 72, such that the needle cover segments 68, 70 and 72 are adapted to pivot relative to one another when the needle cover 60 is moved between the closed and open configurations. To this end, FIG. 8 shows the needle cover 60 in a closed, generally planar configuration with the distal, proximal and intermediate cover segments 68, 70 and 72 completely surrounding, shielding and isolating the cannula 62 so as to prevent an accidental needle strike. FIG. 10 shows the needle cover 60 in an open, expanded configuration to expose the cannula 62 through an opening 74 in the cover to permit the contents of syringe 66 to be injected into a targeted tissue area of the patient.

More particularly, and as best shown in FIG. 9, one of the distal cover segments 68 is pivotally connected at an integral hinge 75 with a first intermediate cover segment 72-1. Intermediate cover segment 72-1 extends continuously from integral hinge 75 to an integral hinge 76 formed with one of the proximal cover segments 70. The other distal cover segment 68 is pivotally connected at an integral hinge 77 with a second intermediate cover segment 72-2. Intermediate cover segment 72-2 is also hingedly connected to the first intermediate cover segment 72-1. A third intermediate cover segment 72-3 is connected from an integral hinge 78 with the other proximal needle cover segment 70 to the first intermediate cover segment 72-1. Each of the proXimal cover segments 70 is also hingedly connected to the hub 64, such that the hub 64 and needle cover 60 are integrally connected together. Each of the distal cover segments 68 is also pivotally connected together at an integral hinge through which the opening 74 is formed for receiving the needle cannula 62.

In the configuration shown in FIG. 9, the hingedly connected distal, proximal and intermediate cover segments 68, 70 and 72 will be aligned with one another to form a figure "8" when the needle cover 60 is collapsed from the closed, planar configuration (of FIG. 8) to the open, expanded configuration (of FIG. 10). The advantage of the hereinabove disclosed arrangement of pivotally interconnected needle cover segments is that the lateral width of needle cover 60 will be minimized relative to the needle covers 1 and 31 of FIGS. 1-7 when said needle cover 60 is located in the open, expanded configuration of FIG. 10 for administering an injection. Accordingly, the needle cover 60, which is characterized by reduced lateral width, will make the process of administering the injection easier and more reliable and permit the health care worker to make a veni puncture through the patient's skin without interfering with the bevel orientation of the cutting surface of cannula 62.

A pair of motion transferring arms 80 project outwardly and in opposite directions from respective proximally oriented needle cover segments 70. Axially and proximally directed (in the direction of the reference arrows 82 of FIG. 9) to cause said arms to rotate, whereby the proximal, distal and intermediate needle cover segments 68, 70 and 72 are correspondingly pivoted around their respective hinges. Hence, the needle cover 60 is moved (in the direction of the reference arrow 84 of FIG. 9) to the open, expanded configuration of FIG. 10 with needle cannula 62 biased in the armed state through opening 74.

The continued application of force to motion transferring arms 78 also causes a locking catch 86, which extends from one of the proximally oriented cover segments 70, to be advanced towards and rotated into a notch 88 formed in one of the distally oriented cover segments 68, whereby catch 86 is snapped into engagement with cover segment 68. Accordingly, the needle cover 60 is shown in FIG. 10 releasably retained in the open, expanded configuration of relatively small lateral width so that an injection may be efficiently administered.

A description of the process for detaching locking catch 86 from the notch 88 and collapsing the needle cover 60 to the closed, generally planar configuration of FIG. 8 with needle cannula 62 in the shielded state (suitable to permit the combination needle cover and cannula to be removed from syringe 66 and safely discarded after use) is similar to the process described when previously referring to FIG. 5. Therefore, this process will not be described again.

FIGS. 11-13 of the drawings illustrate a collapsible needle cover 90 according to a fourth embodiment of the present invention. Needle cover 90 includes a needle cannula 92 and needle supporting hub 94 which are integrally interconnected with needle cover 90 to form a one piece disposable needle cannula and collapsible needle cover that is adapted to be attached to the distal end of a conventional syringe (shown in phantom and represented by reference numeral 96) or removed from the syringe and safely discarded With the cannula 92 surrounded and shielded after use. Needle cover 90 also includes pairs of distally and proximally oriented needle cover segments 97 and 99 which are pivotally interconnected with one another by means of integral hinges. Thus, the needle cover 90 is adapted to be moved between a closed, substantially planar configuration (of FIG. 11) at which to surround and shield the cannula 92, and an open, expanded configuration (of FIG. 13), at which the cannula 92 is exposed through an opening in the needle cover to permit the contents of the syringe 96 to be injected into a targeted tissue area of the patient.

In accordance with the present embodiment, the needle cover 90 is provided with a pair of axially projecting resilient fingers 100 which, as will soon be explained, act as spring locks that cooperate with cannula 92 to releasably retain the needle cover 90 in the open, expanded configuration (of FIG. 13) so that an injection may be administered. Thus, cover 90 can be automatically and reliably locked in the open configuration by means of the fingers 100 without the inclusion of an additional locking catch (such as that designated by reference numeral 16 in FIG. 4).

More particularly, each finger 100 is coextensively formed with and projected outwardly from a respective distal needle cover segment 97. In the closed, planar configuration of FIG. 11, fingers 100 extend in generally spaced, parallel alignment with one another and with the needle cannula 92 which is located therebetween. As the needle cover 90 is moved, in FIG. 12, towards the open, expanded configuration (by means of force transferring arms 102), the fingers 100 will rotate into contact with and slide along needle cannula 92 as the needle cover 90 is positioned in the open, expanded configuration of FIG. 13. That is, the fingers 100 are disposed opposite one another to grip the cannula 92 therebetween, such that the fingers slide axially and proximally along cannula 92 as needle cover 90 is moved to the expanded configuration.

When the needle cover 90 is in the open, expanded configuration of FIG. 13, the distally and proximally oriented needle cover segments 97 and 99 are pivoted relative to one another to assume a swept back, over-center configuration. That is to say, cover segments 97 and 99 are rotated in a generally rearward direction and past a horizontal reference line (designated by reference numeral 104 of FIG. 13). The aforementioned swept back, over-center configuration is achieved by aligning the motion transferring arms 102 in a slightly forward direction (best shown in FIG. 11) and by elongating the integral hinges which connect distal and proximal cover segments 97 and 99 to each other and to the needle supporting hub 94 to permit the continued rearward rotation of the cover segments around their hinges and beyond the horizontal reference line 104. The advantage of the foregoing is that once the needle cover 90 is rotated beyond horizontal reference line 104, the cover segments will easily and continuously rotate around their respective hinges, such that cover 90 is automatically snapped and locked in the open, expanded configuration. The engagement of needle cannula 62 by resilient fingers 100, as such fingers slide axially along the cannula, causes the needle cover 90 to be continuously rotated to and snap-locked in the open configuration, as shown in FIG. 13. Moreover, the resilient fingers 100 form a spring to actively oppose the return of needle cover 90 to the closed configuration of FIG. 11. Therefore, needle cover 90 may be reliably retained in the open, expanded configuration, so that an injection may be administered, without the inclusion of an additional locking catch.

Once the injection has been completed, the health care worker applies a sufficient forward (i.e. axial and distal) pressure to the needle cover 90 to overcome the locking force exerted by resilient fingers 100. Accordingly, the needle cover 90 is moved out of the open configuration and collapsed towards the closed configuration (of FIG. 11), whereby to surround and shield the cannula 92 after use. The needle cover 90 may then be removed from the syringe 96 and safely discarded without subjecting the health care worker to an accidental, and possibly life-threatening, needle strike.

By virtue of the present invention, a reliable, safety enhancing needle cover is available which is integrally connected to a needle cannula and easily manipulated between open and closed configurations, whereby either an injection may be administered or the cannula may be completely surrounded, shielded, and isolated so as to be suitable for disposal after a single use without requiring the needle to be handled, cut or destroyed. Accordingly, a health care worker will not be subjected to the risk of an accidental needle strike and the spread of a contagious and life-threatening disease.

It will be apparent that while the preferred embodiments of the invention have been shown and described, various modifications may be made without departing from the true spirit and scope of the invention. Having thus set forth a preferred embodiment of the invention what is claimed is:

1. For a syringe including a hollow cylinder within which a supply of fluid is to be received and a needle cannula extending from said cylinder and communicating fluidically with the interior thereof, needle cover means being collapsible from an open configuration, at which the cannula projects outwardly therefrom for penetrating the tissue of a patient, to a closed configuration, at which the cannula is surrounded and shielded so as to avoid an accidental needle strike, said needle cover means comprising:

a pair of generally planar, proximal cover segments which, in the closed configuration of said needle cover, are adapted to surround and shield the proximal end of the needle cannula;

a pair of generally planar, distal cover segments which, in the closed configuration of said needle cover, are adapted to surround and shield the distal tip of the cannula;

a pair of generally planar, intermediate cover segments located between said pairs of proximal and distal cover segments and adapted to surround, in the closed configuration of said needle cover, the cannula between the proximal end and distal tip thereof;

each of said pair of distal cover segments having a first end pivotally interconnected with one another and a second end pivotally connected to a respective first end of each of said pair of intermediate cover segments, and each of said pair of proximal cover segments having a first end pivotally interconnected with one another and a second end pivotally connected to a respective second end of each of said pair of intermediate cover segments; and a first hole formed through the first ends of said pair of distal cover segments and a second hole formed through each segment of said pair of intermediate cover segments, said first and second holes being axially aligned with one another and adapted to be coaxially aligned with respect to the needle cannula, such that the cannula projects through said holes and outwardly from said needle cover means when said needle cover means is in the open configuration.

2. The needle cover means for a syringe as recited in claim 1, further comprising hub means to which the first end of each of said pair of proximal cover segments is pivotally connected, said hub means having connection means by which to enable said hub means to be detachably connected to the cylinder of the syringe.

3. The needle cover means for a syringe as recited in claim 1, wherein each planar cover segment of said pairs of proximal and distal cover segments is of identical length relative to one another.

4. The needle cover means for a syringe as recited in claim 1, further comprising a first pair of hinges located respectively between said first end of each of said pair of intermediate cover segments and said second end of each of said pair of distal cover segments by which said pair of distal cover segments are pivotably connected to said pair of intermediate cover segments, and a second pair of hinges located respectively between said second end of each of said pair of intermediate cover segments and said second end of each of said pair of proximal cover segments by which said pair of proximal cover segments are pivotally connected to said pair of intermediate cover segments.

5. The needle cover means for a syringe as recited in claim 1, further comprising catch means extending from a cover segment of said pair of proximal cover segments to engage a cover segment of said pair of distal cover segments to releasably retain said needle cover means in the open configuration.

6. The needle cover means for a syringe as recited in claim 1, further comprising at least one motion transferring arm extending from a cover segment of said pair of proximal cover segments and adapted to be transversely aligned with respect to the longitudinal axis of the cannula, the application of an axial force to said motion transferring arm causing said proximal, distal and intermediate cover segments to pivot relative to one another and said needle cover means to move between said open and closed configurations.

7. The needle cover means for a syringe as recited in claim 1, wherein each cover segment of said pair of intermediate cover segments intersect one another at a location between the respective first and second ends thereof.

8. For a syringe having a hollow cylinder within which a supply of fluid is to be received and a needle cannula extending from said cylinder and communicating fluidically with the interior thereof, needle cover means, including opening means formed at one end for coaxial alignment with respect to the cannula, for collapsing from an open configuration, at which the cannula projects through said opening means for penetrating the tissue of a patient, to a closed configuration, at which the cannula is surrounded and shielded so as to avoid an accidental needle strike, said needle cover means further including said locking means extending from said needle cover means for moving with said needle cover means when said cover means is collapsed to the open configuration, releasably locking said needle cover means in the open configuration so that the cannula projects through said opening means in said cover means, and engaging and gripping the needle cannula at the collapsed, open configuration of said needle cover means to thereby prevent a return of said cover means to the closed configuration.

9. The needle cover means for a syringe as recited in claim 8, wherein said locking means includes locking fingers adapted to extend at opposite sides of the needle cannula so as to be able to slide axially along the needle cannula when said needle cover means is collapsed from the closed to the open configuration, said locking fingers adapted to engage and grip the cannula at the collapsed condition of said needle cover means to prevent a return of said cover means to the closed configuration.

10. The needle cover means for a syringe as recited in claim 8, wherein said needle cover means is split longitudinally and cross sectionally to form a pair of generally planar, proximal cover segments and a pair of generally planar distal cover segments, the cover segments of said distal pair being pivotally interconnected with one another and respective cover segments of said proximal pair so that said cover means extends axially and in generally parallel alignment with the needle cannula in the closed configuration of said cover means, and said cover means extends radially and in transverse alignment with the needle cannula in the open configuration of said cover means.

11. The needle cover means for a syringe as recited in claim 10, wherein said locking means extends from at least one of said pairs of proximal or distal cover segments so that said locking means is rotated into engagement with the needle cannula when said needle cover means is collapsed to the open configuration.

12. The needle cover means for a syringe as recited in claim 10, further including hinge means located between said pairs of proximal and distal cover segments at which each segment of said pair of proximal cover segments is pivotally connected to a respective segment of said pair of distal cover segments so that said cover means is movable between the closed and open configurations.

13. The needle cover means for a syringe as recited in claim 12, wherein said pairs of proximal and distal cover segments are pivotable at said hinge means so that each cover segment thereof is angled proximally of and in substantially the same direction relative to a reference line adapted to extend in perpendicular alignment with the needle cannula.

14. The needle cover means for a syringe as recited in claim 10, further including catch means extending from a cover segment of said pair of distal cover segments to engage the other cover segment from said pair of distal cover segments to retain said cover means in the closed configuration.

15. The needle cover means for a syringe as recited in claim 8, further comprising a hub connected to said cover means and having connection means by which said hub can be detachably connected to the cylinder of the syringe.

16. The needle cover means for a syringe as recited in claim 8, further including a motion transferring arm extending outwardly from said needle cover means and adapted to be transversely aligned with resect to the longitudinal axis of the cannula, the application of an axial directed force to said motion transferring arm causing said cover means to collapse from the closed to the open configuration.

* * * * *